United States Patent
Lee et al.

(10) Patent No.: US 7,829,055 B2
(45) Date of Patent: Nov. 9, 2010

(54) FUNCTIONALIZED NANO-CARBON MATERIALS AND METHOD FOR FUNCTIONALIZING NANO-CARBON MATERIALS THEREOF

(75) Inventors: Chrong-Ching Lee, Tainan County (TW); Kuo-Chen Shih, Kaohsiung (TW); Mei Hua Wang, Miaoli County (TW); Sui-Wen Ho, Tainan (TW); Shu-Jiuan Huang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 976 days.

(21) Appl. No.: 11/645,652

(22) Filed: Dec. 27, 2006

(65) Prior Publication Data

US 2010/0193727 A1    Aug. 5, 2010

(30) Foreign Application Priority Data

Dec. 30, 2005    (TW) .............................. 94147652 A

(51) Int. Cl.
*D01F 9/12*    (2006.01)
*B01J 19/08*    (2006.01)
*C01B 31/02*    (2006.01)

(52) U.S. Cl. ............................... 423/447.1; 423/445 B; 423/447.2; 423/460; 977/737; 977/745; 977/847

(58) Field of Classification Search ... 423/447.1–447.3, 423/445 B, 460; 977/742–754, 842–848
See application file for complete search history.

(56) References Cited

U.S. PATENT DOCUMENTS

| | | | |
|---|---|---|---|
| 5,698,175 A | | 12/1997 | Hiura et al. |
| 5,770,157 A | * | 6/1998 | Cargill et al. ................. 506/40 |
| 5,853,877 A | | 12/1998 | Shibuta et al. |
| 5,861,454 A | | 1/1999 | Ikeda et al. |
| 5,904,190 A | * | 5/1999 | Patel ........................... 141/198 |
| 6,099,965 A | | 8/2000 | Tennent et al. |
| 6,380,434 B1 | * | 4/2002 | Chiang ....................... 564/458 |
| 6,683,783 B1 | * | 1/2004 | Smalley et al. .............. 361/502 |
| 2004/0126303 A1 | * | 7/2004 | Hwang .................... 423/447.2 |
| 2006/0045838 A1 | * | 3/2006 | Malenfant et al. ........ 423/447.1 |

OTHER PUBLICATIONS

Hayashi, et al., NanoTeflons: Structure and EELS Characterization of Fluorinated Carbon Nanotubes and Nanofibers, Nano Letters 2002; 2(5): 491-496.*

(Continued)

*Primary Examiner*—Stanley S. Silverman
*Assistant Examiner*—Daniel C. McCracken
(74) *Attorney, Agent, or Firm*—Birch, Stewart, Kolasch & Birch, LLP

(57) ABSTRACT

A method of functionalizing nano-carbon materials with a diameter less than 1 μm, comprising: contacting the nano-carbon materials with a free radical generating compound such as azo-compound in an organic solvent under an inert gas atmosphere, thereby obtaining nano-carbon materials with functional groups thereon. The physical and chemical properties of the nano-carbon materials can be modified through the aforementioned method.

5 Claims, 2 Drawing Sheets
(1 of 2 Drawing Sheet(s) Filed in Color)

OTHER PUBLICATIONS

Umek, et al., Addition of Carbon Radicals Generated from Organic Peroxides to Single Wall Carbon Nanotubes, Chem. Mater. 2003; 15: 4751-4755 (Nov. 8, 2003.*

Perry's Chemical Engineer's Handbook, p. 2-46 (Don W. Green & James O. Maloney, eds., 7th ed., McGraw-Hill 1997).*

Cameo Chemicals MSDS for Lauroyl Peroxide, accessed at http://cameochemcials.noaa.gov/chemical/963 on Dec. 9, 2009.*

PubChem compound summary for lauroyl peroxide, accessed at http://pubchem.ncbi.nlm.nih.gov/summary/summary.cgi?cid=7773 on Dec. 13, 2009.*

Shen, et al., Structural Disorder and Phase Transformation in Graphite Produced by Ball Milling, Nanostructured Materials 1996; 7(4): 393-399.*

* cited by examiner

FUNCTIONALIZED NANO-CARBON MATERIALS AND METHOD FOR FUNCTIONALIZING NANO-CARBON MATERIALS THEREOF

BACKGROUND OF THE INVENTION

1. Field of the Invention

The invention relates to nano-carbon materials, and more particularly to a method for functionalizing magnetic nano-carbon materials.

2. Description of the Related Art

Nano-carbon materials can be classified as carbon nanotubes, carbon nanofibers, and carbon nanocapsules. Carbon nanotubes comprise hollow tubes, the walls of which are pure carbon with a honeycombed structure similar to graphite. These structures can be multi-walled (MWNTs) or single-walled (SWNTs). Carbon nanocapsules contain multiple graphite layers forming a small spherical capsule inside a larger spherical capsule, making up polyhedral carbon groups. Diameters are around 3~100 nm and outer layers contain the same graphite layer structure as MWNTs. Carbon nanocapsules are also classified into hollow carbon capsules and metal-filled carbon capsules filled with metals, metal oxides, metal carbides, or alloy materials.

Novel nano-carbon materials have potential application in catalysis, polymer composite, and biomedical fields etc. Applications of the nano-carbon materials mainly depend on the degree of the dispersion of the nano-carbon materials into the related medium, such as aqueous phase, organic phase, or polymer materials. Improvements in heat transfer, electrical properties, viscosity, and lubricity, etc. can be realized upon dispersion of the nanotubes. Control of the surface functional groups in the nano-carbon materials is thus important. For example, common nano-carbon materials exhibit hydrophobic properties making it difficult to disperse them in aqueous solution, requiring modification of surface functional groups thereon. To change the surface properties of the nano-carbon materials from hydrophilics to hydrophobics, conventional methods utilize oxidization by strong oxidants or acidification in the strong acid environment. U.S. Pat. No. 5,861,454 discloses the oxidation of fibrils with concentrated nitric acid resulting in a mass, which was difficult to disperse. Hiura and Ebbesen, in U.S. Pat. No. 5,698,175, describe a process for purifying and functionalizing carbon nanotubes, which after synthesis contain carbon impurities such as carbon nanoparticles and amorphous carbons. In this process, the nanotubes are dispersed with ultrasound into nitric acid, chlorosulfonic acid or potassium permanganate in dilute sulfuric acid solution and heated to purify the nanotubes or introduce functional groups into the nanotubes. U.S. Pat. No. 6,099,965 discloses the use of nitric acid ($HNO_3$) to modify the surface functional group on the nano-carbon materials. There are drawbacks associated with the methods now available to provide oxidized carbon nanomaterials. For example, one disadvantage of using strong acid treatment is the generation of environmentally harmful wastes. Treating such wastes increases the cost of the products. Since the condition of acidification is uncontrollable, it is hard to do mass production. The use of strong acid such as nitric acid and sulfuric acid leads to corrosion problems. It would therefore be desirable to provide methods of functionalizing carbon nanotubes which do not use or generate environmentally hazardous chemicals and which can be scaled up easily and inexpensively. While many uses have been found for carbon nanomaterials, as described in the patents and patent applications referred to above, many different and important uses may still be developed if the carbon nanomaterial surfaces can be easily and inexpensively functionalized, permitting interaction of the functionalized carbon nanomaterials with various substrates to form unique compositions of matter with unique properties.

Conventional methods for preparing hydrophilic nano-carbon materials by oxidization or acidification are further limited by unsuitability for magnetic nano-carbon materials. Novel nano-carbon materials such as carbon nanotubes (CNT) and carbon nanocapsules (CNC) filled with metal particles have been developed to apply not only to the separation of the biomedical DNA, RNA, and active enzymes but also to recycling the heavy metal catalysis in the chemical industry. The metal particles of CNT and CNC, however, dissolve in acid, rendering the nano-carbon material to be nonmagnetic.

Therefore, in order that the magnetism of nano-carbon materials is remained, a novel method for functionalizing nano-carbon materials is called for.

BRIEF SUMMARY OF THE INVENTION

Methods for functionalizing nano-carbon materials are provided. An exemplary embodiment of a method for functionalizing nano-carbon materials comprises: a nano-carbon material with a diameter less than 1 μm being provided, and the nano-carbon material, reacting with at least one free radical wherein the free radical is generated from the decomposition of the azo compound.

Functionalized nano-carbon materials are also provided. An exemplary embodiment of a functionalized nano-carbon material has a structure represented by formula (I):

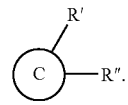

Wherein, Ⓒ is nano-carbon material; R' and R" are the same or different and comprise alkyl group, cyano group, halide, carboxylic acid group and its derivatives, anhydride group, aldehyde group, ketone group, ether group, epoxy group, ester group, amine group amide group, imine group, alkoxy group, hydroxyl group, phosphorus group or aryl group.

A detailed description is given in the following embodiments with reference to the accompanying drawings.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The invention can be more fully understood by reading the subsequent detailed description and examples with references made to the accompanying drawings, wherein.

DETAILED DESCRIPTION OF THE INVENTION

Figure 1:
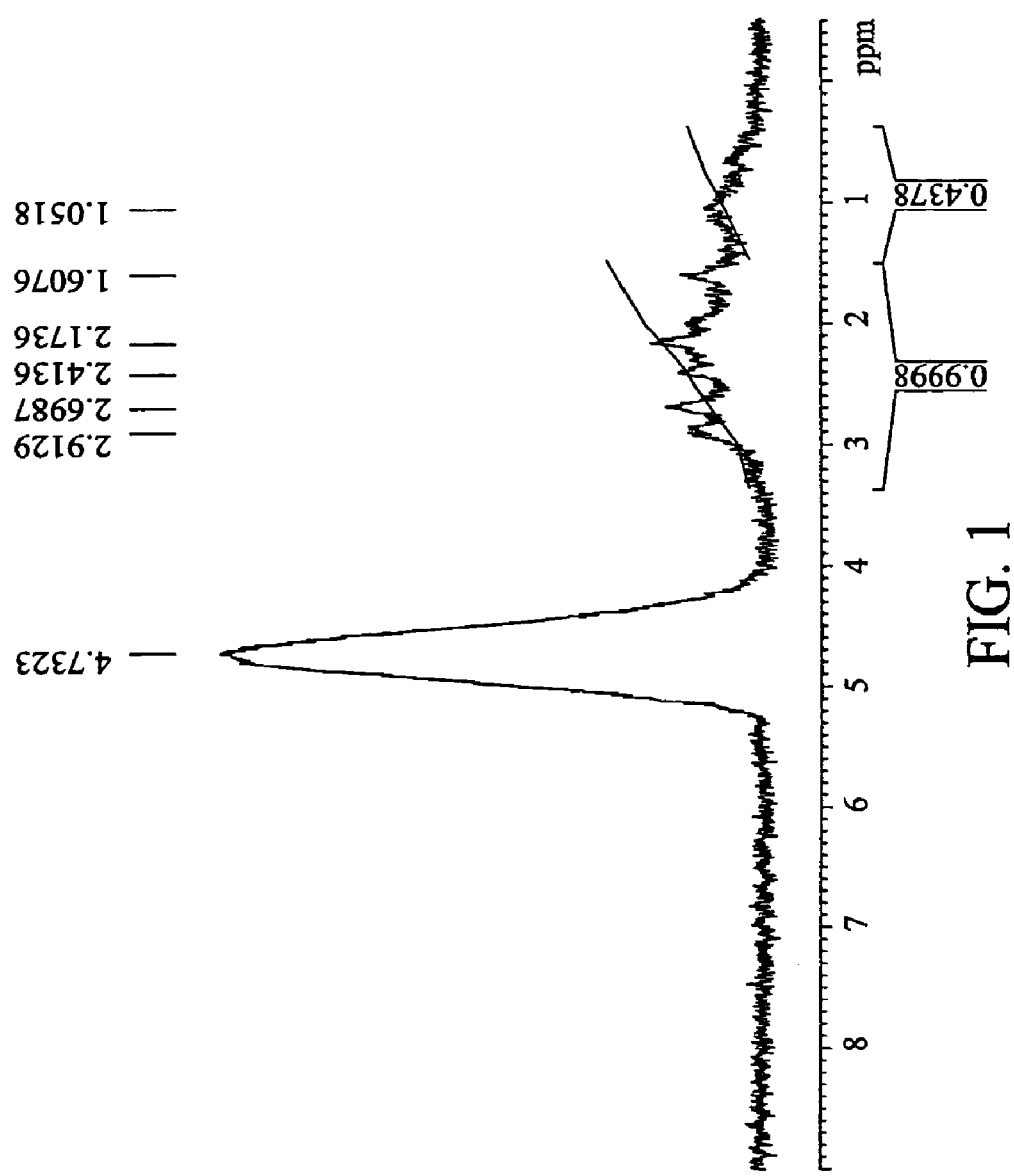
FIG. 1 shows $^1$H-NMR spectrum of the CNT-COOH of Example 1.

The invention provides a method for functionalizing nano-carbon materials with simplified steps, suitable for mass production. Further, magnetic nano-carbon materials can be functionalized by the method without the use of oxidizer or strong acid, thus retaining the magnetic properties thereof.

The method for functionalizing nano-carbon materials comprises reacting a free radical compound with a nano-carbon material at a specific reaction temperature (depending upon the half-life of the free radical compound) under an inert gas atmosphere.

In an exemplary embodiment of the invention, the nano-carbon materials are modified to bond with hydrophilic groups (such as carboxylic groups) and easily dispersible in water. Since conventional methods such as acid treatment employ water as solvent, it is difficult to isolate the products with hydrophilic groups on the surface without loss, thus unsuitable for mass production. In the invention, the nano-carbon material can be reacted with the free radical compound in an organic solvent, resulting in a grafting reaction. The obtained hydrophilic nano-carbon material can be easily separated from the organic solvent without a significant loss, making it much easier for mass production. Suitable organic solvent can be any one which can dissolve free radical compounds, such as ethyl acetate, benzene, toluene, tetrahydrofuran, etc., or combinations thereof.

The nano-carbon material has a diameter less than 1 μm and can be carbon nanotubes, carbon nanocapsules, active carbon or carbon fiber.

The carbon nanotubes can be single-layer or multi-layer carbon nanotubes and have a tube diameter less than 1 μm. The carbon nanocapsules can have singular or multiple graphite layers and a diameter less than 1 μm. The nano-carbon material can be hollow or filled with metal, or metal compound, such as metal oxide, metal carbide, metal sulfide, metal nitride, metal borate, or alloy. Suitable metals or metallines can comprise, without being limited to, Sc, V, Cr, Fe, Co, Ni, Cu, Y, Zr, Mo, Ru, Rh, Pd, La, Ce, Pr, Nd, Gd, Tb, Dy, Ho, Er, Tm, Lu, Ta, Os, Ir, Pt, Au, Th, U, or combinations thereof.

The inert gas atmosphere can comprise nitrogen gas, argon gas, helium gas, neon gas, or combinations thereof.

The free radical generating compound can be a peroxide or azo compound, and comprises 2,2'-azobis(2-cyano-2-butane), dimethyl 2,2'-azobis(methyl isobutyrate), 4,4'-azobis (4-cyanopentanoic acid), 4,4'-azobis(4-cyanopentan-1-ol), 1,1'-azobis(cyclohexane carbonitrile), 2-(t-butylazo)-2-cyanopropane, 2,2'-azobis[2-methyl-(N)-(1,1)-bis(hydroxymethyl)-2-hydroxyethyl]propionamide, 2,2'-azobis[2-methyl-N-hydroxyethyl)]propionamide, 2,2'-azobis(N,N'-dimethyleneisobutyramidine) dihydrochloride, 2,2'-azobis (2-amidinopropane) dihydrochloride, 2,2'-azobis (N,N'-dimethyleneisobutyramine), 2,2'-azobis(2-methyl-N-[1,1-bis(hydroxymethyl)-2-hydroxyethyl]propionamide, 2,2'-azobis(2-methyl-N-[1,1-bis(hydroxymethyl)ethyl] propionamide], 2,2'-azobis[2-methyl-N-(2-hydroxyethyl) propionamide], 2,2'-azobis(isobutyramide)dihydrate, 2,2'-azobis(2,2,4-trimethylpentane), 2,2'-azobis (2-methylpropane), dilauroyl peroxide, tertiary amyl peroxides, tertiary amyl peroxydicarbonates, t-butyl peroxyacetate, t-butyl peroxybenzoate, t-butyl peroxyoctoate, t-butyl peroxyneodecanoate, t-butylperoxy isobutyrate, t-amyl peroxypivalate, t-butyl peroxypivalate, di-isopropyl peroxydicarbonate, dicyclohexyl peroxydicarbonate, dicumyl peroxide, dibenzoyl peroxide, potassium peroxydisulfate, ammonium peroxydisulfate, di-tert butyl peroxide, di-t-butyl hyponitrite, dicumyl hyponitrite or combinations thereof. The aforementioned free radical compound does not remove the metal component of the nano-carbon materials, allowing the magnetism thereof to be retained after functionalization.

The functionalized nano-carbon material has a structure represented by formula (I):

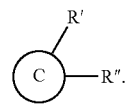

Wherein © is nano-carbon material; and R' and R" are the same or different and comprise alkyl group, cyano group, halide, acid group, aldehyde group, ketone group, ether group, epoxy group, ester group, amide group, alkoxy group, or aryl group.

Preparation of Functionalized Magnetic Nano-Carbon Particles

Example 1

1 g nano-carbon particle (comprising: 96.7% carbon, 2.4% iron, 0.9% alumina), 0.56 g 4,4'-Azobis 4-cyanovaleric acid ((sold and manufactured under the trade number of Vazo 68), and 20 ml ethyl acetate (EA) were added into a bottle in a nitrogen atmosphere with ultrasonic agitation for 15 min. After stirring for 16 hours at 60° C., the resulting solution was filtered and the solid collected, washed with ethyl acetate, and dried, giving a functionalized product CNT-COOH.

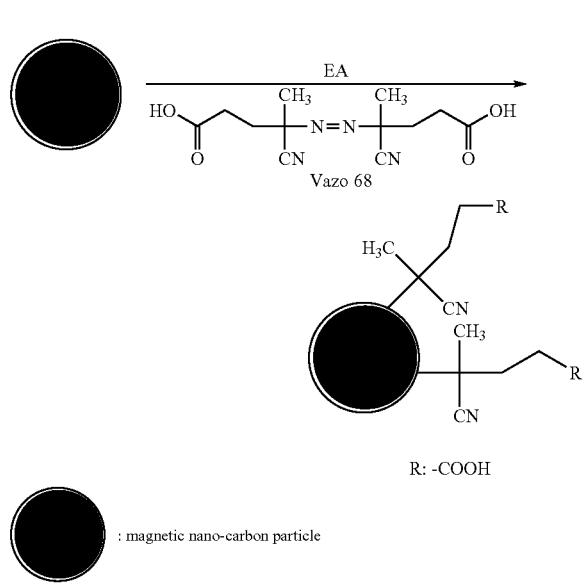

The 1H-NMR spectrum of CNT-COOH was shown in FIG. 1. The peaks with chemical shift of 1~0.3 ppm shown the hydrogen singles of functional group (—COOH) of CNT-COOH. The peak with chemical shift of 4.7323 ppm shows the hydrogen single of solvent D2O.

The product CNT-COOH tended to mass together, rather than dispersing in EA, thereby being more easily purified.

The functional group concentration of CNT-COOH was then measured by following steps. 50 mg CNT-COOH and 100 ml water were added into a bottle. After stirring for 30 min, 0.2 ml NaOH (0.1N) was added into the bottle and mixed with ultrasonic agitation, with resulting pH of the mixture 9.79. HCl aqueous solution (0.00909N) was added into the mixture, until the pH of carbon nanocapsules approached less than 7 (6.8). Since the consumption of the HCl aqueous solution was 1.55 ml (0.0140895 mmol), the carboxylic group concentration of 1 g CNT was estimated at 0.1177 mmol.

The functional group concentration was then determined by thermo gravimetric analysis (TGA). During measurement, the weight of CNT-COOH was slightly reduced at 250° C., equaling a functional group concentration of 0.1 mmol/g.

Comparative Example 1

Comparative example 1 was performed as Example 1 except for omitting the use of 4,4'-Azobis 4-cyanovaleric acid, giving a product CNT-B.

Nano-Carbon Material Hydrophilic Test

Example 2

Figure 2:
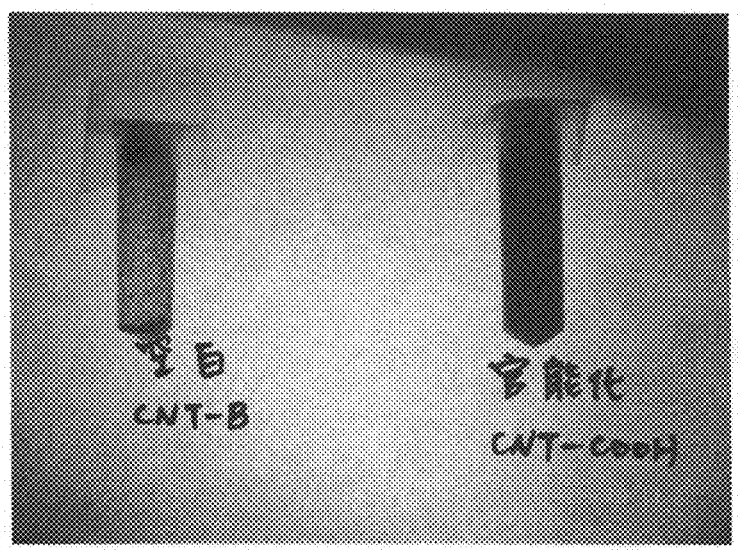
FIG. 2 shows dispersion of conventional nano-carbon materials in water.

50 mg CNT-COOH and 50 mg CNT-B were respectively added into 100 ml water and stirred with ultrasonic agitation for 30 min. After standing for 1 day, the dispersion degrees of nano-carbon materials were observed, as shown in FIG. 2. Accordingly, the functionalized nano-carbon material CNT-COOH was uniformly dispersed in water. While the unfunctionalized nano-carbon materials CNT-B precipitated and would not uniformly disperse in water.

Figure 3:
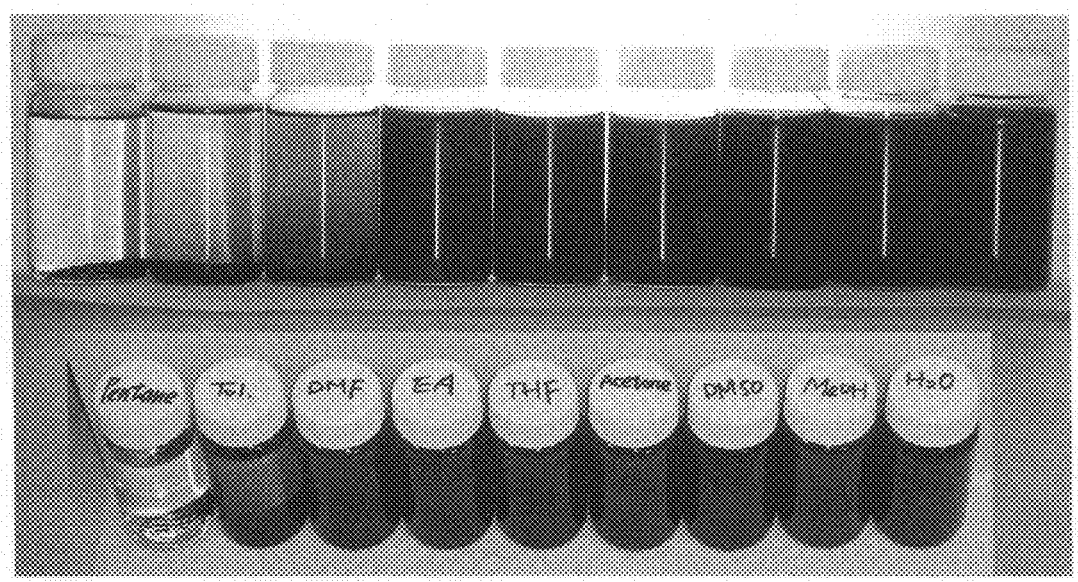
FIG. 3 shows dispersion of the CNT-COOH of Example 1 in various solvents.

Solvent Dispersion Test for CNT-COOH 50 mg CNT-COOH were respectively added into 100 ml bottles filled with pentane, toluene, DMF, EA, THF, acetone, DMSO, methanol, and water, and the mixtures were stirred for 30 min. After standing for 3 days, the dispersion degree of each bottle was observed, as shown in FIG. 3. Accordingly, CNT-COOH was uniformly dispersed into EA, THF, acetone, DMSO, methanol, and water without gathering together, despite standing for 1 month.

Magnetism Measurement of CNT-COOH

Magnetism of functionalized carbon nano-tube was determined by Vibrating Sample Magnetometer (VSM). When a material is placed within a uniform magnetic field and made to undergo sinusoidal motion, there is some magnetic flux change. This induces a voltage in the pick-up coils, which is proportional to the magnetic moment of the sample.

TABLE 1

The VSM data of a variety of carbon nanotubes.

| Sample | Coercivity (Hci) | Magnetization | Mass |
|---|---|---|---|
| Original | 88.31 G | 3.622 emu/g | 10.30E−3 g |
| Vazo 68 treatment | 90.31 G | 2.929 emu/g | 12.20E−3 g |
| $HNO_3$ treatment* | 14.62 G | 0.540 emu/g | 24.40E−3 g |

*conc. $HNO_3$, reflux for 12 hr.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of functionalizing nano-carbon materials having a diameter less than 1 μm, comprising:

contacting the nano-carbon materials with a free radical generating compound in an organic solvent at a temperature range between 25~150° C. under an inert gas atmosphere and thereby producing functionalized nano-carbon materials, wherein the free radical compound comprises 2,2'-azobis(2-cyano-2-butane), dimethyl 2,2'-azobis(methyl isobutyrate), 4,4'-azobis(4-cyanopentanoic acid), 4,4'-azobis(4-cyanopentan-1-ol), 1,1'-azobis(cyclohexane carbonitrile), 2-(t-butylazo)-2-cyanopropane, 2,2'-azobis[2-methyl-(N)-(1,1)-bis(hydroxymethyl)-2-hydroxyethyl]propionamide, 2,2'-azobis[2-methyl-N-hydroxyethyl)]propionamide, 2,2'-azobis(N,N'-dimethyleneisobutyramidine) dihydrochloride, 2,2'-azobis(2-amidinopropane) dihydrochloride, 2,2'-azobis (N,N'-dimethyleneisobutyramine), 2,2'-azobis(2-methyl-N-[1,1-bis(hydroxymethyl)-2-hydroxyethyl]propionamide, 2,2'-azobis(2-methyl-N-[1,1-bis(hydroxymethyl)ethyl] propionamide), 2,2'-azobis[2-methyl-N-(2-hydroxyethyl) propionamide], 2,2'-azobis (isobutyramide)dihydrate, 2,2'-azobis(2,2,4-trimethylpentane), 2,2'-azobis (2-methylpropane), or combinations thereof.

2. The method as claimed in claim 1, wherein the nano-carbon material comprises single-layer or multi-layer carbon nanotubes with a diameter less than 1 μm.

3. The method as claimed in claim 1, wherein the nano-carbon material comprises carbon nanocapsules with a diameter less than 1 μm, wherein the carbon nanocapsules have singular or multiple graphite layers.

4. The method as claimed in claim 1, wherein the nano-carbon material is filled with metal, metal oxide, metal carbide, metal sulfide, metal nitride, metal borate, or alloy.

5. The method as claimed in claim 4, wherein the metal comprises Sc, V, Cr, Fe, Co, Ni, Cu, Y, Zr, Mo, Ru, Rh, Pd, La, Ce, Pr, Nd, Gd, Tb, Dy, Ho, Er, Tm, Lu, Ta, Os, Ir, Pt, Au, Th, U, or combinations thereof.

* * * * *